May 11, 1948. R. L. STONER Plant Pat. 798

PEACH TREE

Filed Nov. 20, 1946

INVENTOR
RUSSELL L. STONER
BY Henry G. Sylvester
HIS ATTORNEY

Patented May 11, 1948

Plant Pat. 798

UNITED STATES PATENT OFFICE

798

PEACH TREE

Russell L. Stoner, near Dayton, Ohio

Application November 20, 1946, Serial No. 711,168

1 Claim. (Cl. 47—62)

This invention relates to a new variety of peach tree originating as a bud sport from the Early Elberta peach tree. This new variety has been thoroughly tested in the south central part of Ohio. The fruit matures exactly at the same time as the Early Elberta. Near Dayton, Ohio, where the new fruit has been tested, it has been found to ripen about five days later than the Champion and about five days ahead of the Georgia Belle.

The fruit size and shape are identical with the strain of Early Elberta, from which it was developed as a bud sport. The skin of the fruit is of a cream color, with a mottled flaming red blush. The blush varies from a light pink to a dark red. At maturity the fruit is covered from one-fourth to three-fourths with red. The cream background of the flesh is somewhat darker than the Georgia Belle. The flesh is firm, excellent in quality and the stone is always free. The variety is reproduced asexually and the characteristics of the fruit hold true through succeeding propagations.

In the drawings,

Figure 1 discloses two peaches viewed from opposite ends.

Figure 1:
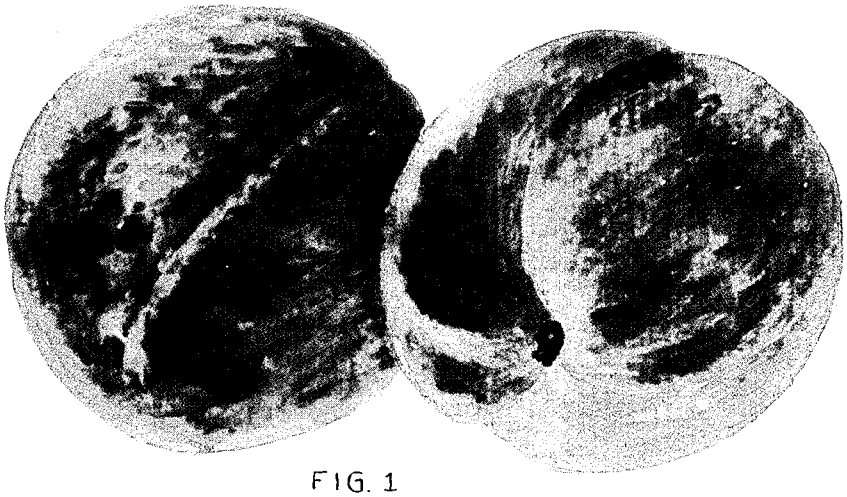
Figure 2:
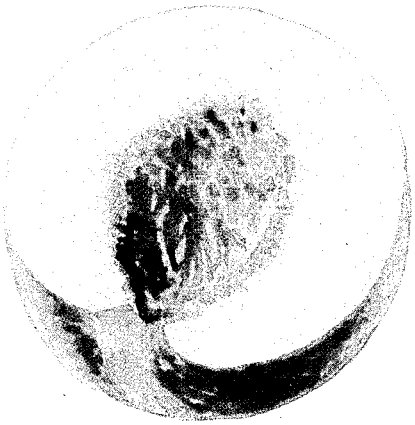
Figure 2 is a cross sectional view showing the stone removed.
Figure 3:
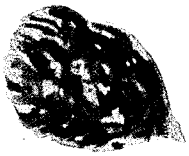
Figure 3 is a side elevational view of the stone.
Figure 4:
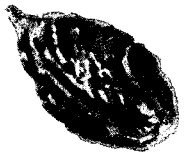
Figure 4 is an end view of the stone.
Figure 5:
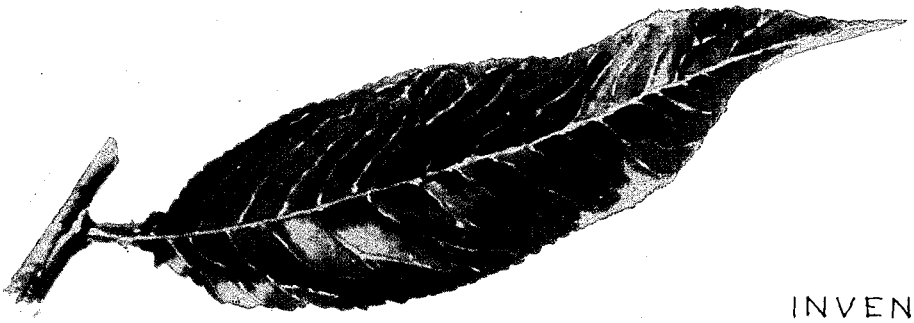
Figure 5 is a view of a leaf, depicting its color and other characteristics.

The following is a detail description of a new variety of peach. The specimens illustrated in the drawings were grown near Dayton, Ohio.

Tree: The tree is large, vigorous, upright, spreading, dense topped, hardy, very productive. This variety is a very vigorous grower.

Leaves: The leaves are six inches long and three-fourths inch wide, oval to obovate lanceolate; upper surface dull, dark olive green; margins finely to coarsely serrated.

Flower: The flower buds are large, pubescent, conical to obtuse, plump, appressed; flowers appear in mid-season; blossoms light pink near the centre, dark pink towards the edges, one and one-fourth inches across; petals short, glabrous green; calyx tube reddish green, orange color within, pubescent without, petals oval to ovate, bluntly notched near the base, filaments one and one-half inches long, shorter than petals, pistil pubescent at the ovary, larger than the stamens, self fertile.

Fruit: The fruit matures exactly with the time of the Early Elberta. On a farm located eight miles north of Dayton, Ohio, the fruit ripened about five days later than the Champion and five days ahead of the Georgia Belle.

The fruit size and shape are identical with the strain of Early Elberta, from which it developed as a bud sport. Fruit is two and one-half inches wide and two and three-fourths inches long. A great many fruits have a diameter of three inches.

The fruit is roundish oblong, with a slight bulge on one side. The cavity is deep, abrupt to flaring, always mottled with red; suture is shallow, slightly deepening toward the apex; apex roundish, with a pointed tip; color cream, with a mottled flaming red blush; blush varies from a light pink to a dark red. At maturity fruits are from one-fourth to three-fourths covered with red. The cream background is somewhat darker than the Georgia Belle, finely pubescent. The skin is thick and tough. At maturity the skin can easily be pulled away from the flesh. Flesh is cream colored, about plate 9–D–2, page 41, of Maerz and Paul's Dictionary of Color, somewhat darker than the Georgia Belle, firm, excellent in quality; stone always free. Stone is one and eleven-sixteenths inches long and one inch thick, wide, broadly ovate, usually plump, pointed and somewhat bulging one one side, with pitted surfaces.

*Distinctive features of the peach*

(1) Always free.

(2) Size and shape the same as Early Elberta.

(3) Toughness of skin, firmness of flesh the same as Early Elberta.

(4) Has proven hardy on said farm. Twelve crops in the last thirteen years.

(5) Resembles Early Elberta in tree, leaf and flower characteristics.

(6) Differs from the Early Elberta in that it has a cream colored flesh and is much hardier.

This variety has been reproduced through three generations asexually by budding and has remained consistent in size, color and quality.

*History of peach*

In 1929, in the orchard of Early Elbertas growing on a farm eight miles north of Dayton, Ohio, one limb of an Early Elberta was found bearing cream-colored peaches. This limb was about eighteen inches above the ground and well above the union of bud and stock. Hence, there is every reason to believe that it is a bud sport.

In the fall of 1930 a few of these trees were budded. These were planted in 1931. In 1931 more trees were budded. These were planted in 1932. These two plantings made an orchard of 63 trees. These plantings missed only one crop since that time. The severe winter of 1935 and 1936 killed the buds.

I claim:

A new and distinct variety of peach tree substantially as herein disclosed, characterized as to novelty by the tough, thick skin that is easily pulled away from the flesh and the creamy color of the flesh somewhat darker than the Georgia Belle, the flesh being firm and excellent in quality, the stone always free, and the regular production each season of fruit uniform in size.

RUSSELL L. STONER.